United States Patent [19]

Ikeda et al.

[11] Patent Number: 4,582,622
[45] Date of Patent: Apr. 15, 1986

[54] MAGNETIC PARTICULATE FOR IMMOBILIZATION OF BIOLOGICAL PROTEIN AND PROCESS OF PRODUCING THE SAME

[75] Inventors: Mikio Ikeda; Shiro Sakamoto, both of Tokyo; Kazumasa Suzuki, Saitama, all of Japan

[73] Assignee: Fujirebio Kabushiki Kaisha, Tokyo, Japan

[21] Appl. No.: 660,462

[22] Filed: Oct. 12, 1984

[51] Int. Cl.$^4$ ............................ H01F 1/00; H01F 1/28; C04B 35/64
[52] U.S. Cl. .................................. 252/62.53; 260/117
[58] Field of Search ..................... 260/117; 252/62.53

[56] References Cited

U.S. PATENT DOCUMENTS 4,416,813  11/1983  Ikeda et al. ........................ 260/117
4,519,931  5/1985   Soga et al. ........................ 252/62.53

Primary Examiner—Arthur P. Demers
Attorney, Agent, or Firm—Burgess, Ryan & Wayne

[57] ABSTRACT

A magnetic particulate comprising gelatin, water-soluble polysaccharide, sodium polymetaphosphate and ferromagnetic substance, which is used as a carrier for immobilization of biological proteins such as antigens, antibodies or enzymes, and a process of producing the magnetic particulate.

15 Claims, No Drawings

MAGNETIC PARTICULATE FOR IMMOBILIZATION OF BIOLOGICAL PROTEIN AND PROCESS OF PRODUCING THE SAME

The present invention relates to a magnetic particulate and a process of producing the same. The magnetic particulate is a particulate having magnetic character and can be attracted by a magnet. The magnetic particulate of the present invention is used as a carrier to immobilize biological proteins such as antigens, antibodies or enzymes. Immobilized antigens, antibodies or enzymes are used in assays involving antigen-antibody reaction.

Particulates comprising organic polymers as principal ingredients have been proposed, which can be used as the carrier as stated above, and one of the inventors of this invention has proposed a particulate (particle) comprising gelatin, water-soluble polysaccharide and sodium polymetaphosphate (Japanese Patent Publication for public inspection Nos. 153658/1982 and 160465/1982: European Patent Application No. 82301235.6 (0062968); U.S. Pat. No. 4,416,813; Spanish Pat. No. 510433).

It is an object of the present invention to provide a particulate having magnetic character. The magnetic particulate can be produced by admixing fine particles of ferromagnetic substance with a particulate comprising organic polymers.

The magnetic particulate has advantages as shown below when it is used as a carrier for immobilization of biological protein:

(1) Agglutination time in an antigen-antibody reaction can be controlled by a magnet.

(2) Magnetic particulates can be easily separated or recovered from a suspension thereof by magnet force, compared with conventional particulates not containing magnetic substances.

A process of providing a magnetic particulate has been proposed by K. Widder et al, which comprises covering a magnetic particle by human serum albumin and then repeating emulsification and heat treatment of it (referring to K. Widder, G. Flouret and A. Senyei: *J. Pharm. Sci.* 68, 79 (1979)). Widder's process has a disadvantage that it is difficult to get homogeneous magnetic particulates.

The inventors of this invention found that homogeneous magnetic particulates can be obtained by admixing fine particles of ferromagnetic substance with a particulate comprising gelatin, a water-soluble polysaccharide and sodium polymetaphosphate. The present invention is based on this discovery.

The magnetic particulate of this invention comprises 5–30% by weight of gelatin, 1–5% by weight of a water-soluble polysaccharide, 0.01–1% by weight of sodium polymetaphosphate, 0.00001–2% by weight of a colloidal ferromagnetic substance and 62–94% by weight of water, having a particle size of 0.8–50 μm and being water-insoluble and hydrophilic. The gelatin of the particulate has been cross-linked with aldehyde between amino groups thereof.

In this invention, gelatin having a molecular weight of about 100,000 and an isoelectric point at a pH of between 8.4 and 9.1 is used. The preferred polysaccharide is gum arabic, but carboxymethyl cellulose, sodium alginate and agar also can be used in this invention. Sodium polymetaphosphate having the formula $(NaPO_3)_n$ wherein n is an integer of 3 to 6, can be preferably used. Ferromagnetic substances include ferrites having the formula $MFe_2O_4$ wherein M represents a divalent metal such as $Fe^{++}$, $Mn^{++}$, $Cu^{++}$, $Ni^{++}$ or $Co^{++}$. In the process of producing a magnetic particulate of this invention, the ferrites are used in an aqueous suspension form containing colloidal ferrites in an amount of about 30% w/v.

An aqueous suspension colloid of magnetite ($Fe_3O_4$), which is used in this invention, can be prepared by the steps of: mixing 100 ml of a 1M $FeCl_2$ solution and 100 ml of a 2M $FeCl_3$ solution, adding 200 ml of a 6N NaOH solution to the mixture to produce a precipitate, washing the precipitate with hot water and dispersing the precipitate in 100 ml of an aqueous solution (about 0.1% w/v) of a surfactant such as sodium oleate.

An aqueous suspension colloid of a ferrite, e.g. $MnFe_2O_4$, can be prepared by the steps of: mixing 100 ml a 1M $MnCl_2$ solution and 100 ml of a 2M $FeCl_3$ solution, adding dropwise a 6N NaOH solution to the mixture until the solution has the pH of 11, heating the mixture at 100° C. for 30 minutes, washing the precipitate with hot water and dispersing the precipitate in about 100 ml of an aqueous solution (about 0.1% w/v) of a surfactant such as sodium oleate.

Aqueous suspension colloids of other ferrites, i.e. $CuFe_2O_4$, $NiFe_2O_4$ and $CoFe_2O_4$, can be prepared by repeating the procedure of preparing the aqueous suspension of $MnFe_2O_4$ as shown above, except that $CuCl_2$, $NiCl_2$ and $CoCl_2$ are used instead of $MnCl_2$, respectively, and the reaction mixture is heated at higher temperatures than 100° C. in an oil bath or an autoclave.

An aqueous suspension colloid of the ferrites is prepared to contain colloidal ferrite in an amount of about 30% w/v.

The magnetic particulate of the present invention can be produced as follows:

0.01 to 2 g of gelatin, 0.01 to 2 g of water-soluble polysaccharide, 0.001 to 2 g of sodium polymetaphosphate and 0.01 to 5 g of colloidal ferrite (about 36 μl to 18 ml of aqueous suspension colloid of ferrite) are added into 100 ml of an aqueous solution containing about 0.1% (w/v) anionic or nonionic surfactant to produce a colloidal solution, and after the pH of the colloidal solution was adjusted to 2.5 to 6.0 with an acid such as acetic acid, the gelatin is cross-linked with an aldehyde at temperatures of 5° C. to 35° C. with stirring.

The anionic surfactant includes alkylsulfosuccinates, alkylsulfomaleates, alkylsulfuric acid esters and polyoxyethylene alkyl ether sulfuric acid esters. The nonionic surfactant includes polyoxyethylene fatty acid esters, polyoxyethylene alkyl ethers, polyoxyethylene alkyl phenyl ethers and polyethylene glycol fatty acid esters, wherein the alkyl group for both groups of surfactants has 6 to 25 carbon atoms.

Aldehyde for cross-linking gelatin includes glutaraldehyde and formaldehyde.

The present invention is further illustrated by the following examples.

EXAMPLE 1

One gram of gelatin having an isoelectric point at a pH of 9 was dissolved in 25 ml of water at 40° C. and to this solution was added a 10% NaOH solution to adjust the pH to 9.0, and then to this solution was added a solution of 1 g of gum arabic in 20 ml of water at 40° C. This mixture was poured into 150 ml of a 30% ethanol solution, and after stirring, to this mixture were added 0.8 ml of a 10% sodium hexametaphosphate solution, 1 ml of a 1% alkylsulfomaleate (trade name: Demol Ep, manufactured by Kao Soap Co.) solution and 60 μl of a suspension colloid of $Fe_3O_4$ prepared above, and the mixed solution was sufficiently stirred. Subsequently, a 10% acetic acid solution was added dropwise to the mixture while it was kept at 40° C. and the pH of the mixture was adjusted to 4.8 to form particulates. The suspension of the particulates was cooled to 5° C. in an ice bath, and 0.65 g of glutaraldehyde was added to the suspension. After stirring, the suspension was allowed to stand at 5° C. overnight. Then, the suspension was centrifuged at 2000 rpm for 10 minutes, and the resulting particulates were collected. The particulates were suspended in a 0.005% Demol Ep solution, and the suspension was centrifuged again. This washing procedure was repeated three times, and the particulates were suspended in 50 ml of a 4% formaldehyde solution, and this suspension was allowed to stand at 5° C. for one week.

In this manner, a suspension of magnetic particulates comprising about 20% of gelatin, about 2% of gum arabic, about 0.1% of $(NaPO_3)_6$, about 0.001% of $Fe_3O_4$ and about 78% of water, and having particle size of about 3 μm was obtained.

EXAMPLE 2

The same procedure employed in Example 1 was repeated except that sodium trimetaphosphate and 600 μl of a suspension colloid of $MnFe_2O_4$ prepared above were used instead of sodium hexametaphosphate and 60 μl of a suspension colloid of $Fe_3O_4$.

In this manner, a suspension of magnetic particulates comprising about 20% of gelatin, about 2% of gum arabic, about 0.1% of $(NaPO_3)_3$, about 0.005% of $MnFe_2O_4$ and about 78% of water, and having particle size of about 3.5 μm was obtained.

Magnetic particulates in powder form can be obtained by removing water from the suspension of magnetic particulates and lyophilizing the wet magnetic particulates.

In Examples 1 and 2, suspensions of magnetic particulates containing 0.001% and 0.005% of ferromagnetic substance and having particle sizes of about 3 μm and about 3.5 μm were obtained. It is understood, however, the composition of the magnetic particulate can be changed by changing the amount of the ingredients to be used in the production. Further, the particle size of the magnetic particulate can be somewhat changed by producing the magnetic particulate in different conditions of temperature and pH of the solution or a different method of stirring of the solution.

What is claimed is:

1. A magnetic particulate for immobilization of biological proteins which comprises 5% to 30% by weight of gelatin, 1% to 5% by weight of a water-soluble polysaccharide, 0.01% to 1% by weight of sodium polymetaphosphate having the formula $(NaPO_3)_n$, 0.00001% to 2% by weight of ferromagnetic substance and 62% to 94% by weight of a water.

2. The magnetic particulate of claim 1, wherein said gelatin has an isoelectric point at a pH value between 8.4 and 9.1.

3. The magnetic particulate of claim 1, wherein said water-soluble polysaccharide is selected from the group consisting of gum arabic, carboxymethyl cellulose, sodium alginate and agar.

4. The magnetic particulate of claim 1, wherein said sodium polymetaphosphate has the formula $(NaPO_3)_n$ wherein n is an integer of 3 to 6.

5. The magnetic particulate of claim 1, wherein said ferromagnetic substance is a ferrite having the formula $MFe_2O_4$ wherein M is a divalent metal selected from the group consisting of $Fe^{++}$, $Mn^{++}$, $Cu^{++}$, $Ni^{++}$ and $Co^{++}$.

6. A process for producing a magnetic particulate for immobilization of biological proteins which comprises the steps of: preparing an aqueous colloidal solution containing gelatin, a water-soluble polysaccharide, sodium polymetaphosphate and ferromagnetic substance, adjusting the pH of said colloidal solution to between 2.5 and 6.0 with an acid, and forming a water-insoluble particulate by adding an aldehyde to said colloidal solution.

7. The process of claim 6, wherein said gelatin has an isoelectric point at a pH value between 8.4 and 9.1.

8. The process of claim 6, wherein the concentration of gelatin is between 0.01% and 2% by weight of said colloidal solution.

9. The process of claim 6, wherein the concentration of water-soluble polysaccharide is between 0.01% and 2% by weight of said colloidal solution.

10. The process of claim 9, wherein said water-soluble polysaccharide is selected from the group consisting of gum arabic, carboxymethyl cellulose, sodium alginate and agar.

11. The process of claim 6, wherein the concentration of sodium polymetaphosphate is between 0.001% and 2% by weight of said colloidal solution.

12. The process of claim 11, wherein said sodium polymetaphosphate has the formula $(NaPO_3)_n$, wherein n is an integer of from 3 to 6.

13. The process of claim 6, wherein said ferromagnetic substance is present in an amount between 0.01% and 5% by weight of said colloidal solution.

14. The process of claim 13, wherein said ferromagnetic substance is a ferrite having the formula $MFe_2O_4$, wherein M is a divalent metal selected from the group consisting of $Fe^{++}$, $Mn^{++}$, $Cu^{++}$, $Ni^{++}$ and $Co^{++}$.

15. The process of claim 6, wherein said aldehyde is selected from the group consisting of glutaraldehyde and formaldehyde.

* * * * *